United States Patent [19]

Van Veen et al.

[11] Patent Number: 4,889,427
[45] Date of Patent: Dec. 26, 1989

[54] METHOD AND APPARATUS FOR DETECTING LOW CONCENTRATIONS OF (BIO) CHEMICAL COMPONENTS PRESENT IN A TEST MEDIUM USING SURFACE PLASMON RESONANCE

[75] Inventors: Jacobus J. F. Van Veen, Amsterdam; Johan W. Konig, Noordwijk; Willem M. Ter Kuile, Delft; Cornelis Van Dijk, Bennekom, all of Netherlands

[73] Assignee: Nederlandse Organisatie Voor Toegepastnatuurwetenschappelijk Onderzoek Tno, The Hague, Netherlands

[21] Appl. No.: 180,156

[22] Filed: Apr. 11, 1988

[30] Foreign Application Priority Data

Apr. 10, 1987 [NL] Netherlands ................... 8700851

[51] Int. Cl.$^4$ .............................................. G01N 21/55
[52] U.S. Cl. ................................................ 356/445
[58] Field of Search ....................................... 356/445

[56] References Cited

PUBLICATIONS

Gordon et al., "Surface Plasmons as a Probe of the Electrochemical Interface", *Surface Science*, 101: 499-506 (1980).
Oda et al., "Instantaneous Observation of Angular Scan-Attenuated Total Reflection Spectra", *Optics Communications*, vol. 59, Nos. 5, 6, pp. 361-365 (Oct. 1986).
Foley et al., "In Situ Infrared Spectroelectrochemistry", *Analytical Chemistry*, vol. 57, No. 8, pp. 945(A)-956(A) (Jul. 1985).
Ashley et al., "Modulated Surface Vibrational Spectroscopy at the Electrode-Solution Interface", *Trends in Analytical Chemistry*, vol. 4, No. 6, pp. 142-145 (1985).

*Primary Examiner*—Vincent P. McGraw
*Attorney, Agent, or Firm*—Brumbaugh, Graves, Dononhue & Raymond

[57] ABSTRACT

A method and an apparatus for detecting low concentrations of at least one (bio-) chemical component present in a test medium in a test cell, having a metal layer as sub wall with an external glass prism, using the surface plasmon resonance effect. A light ray is coupled in and, after attenuated total reflection, is coupled out and the intensity thereof is measured. The incidence angle position of the resonance curve is determined under the influence of the change, caused by the component, in the dielectric constant of the test medium near the metal layer. An adjustable selector is applied to the metal layer, in order to influence the incidence angle position of the resonance curve, through which the concentrations or concentration changes of one or more components in the test medium can be simultaneously determined through one or more differential measurements. A preferential association and therefor a higher concentration at the metal layer of one component above another is brought about.

12 Claims, 8 Drawing Sheets

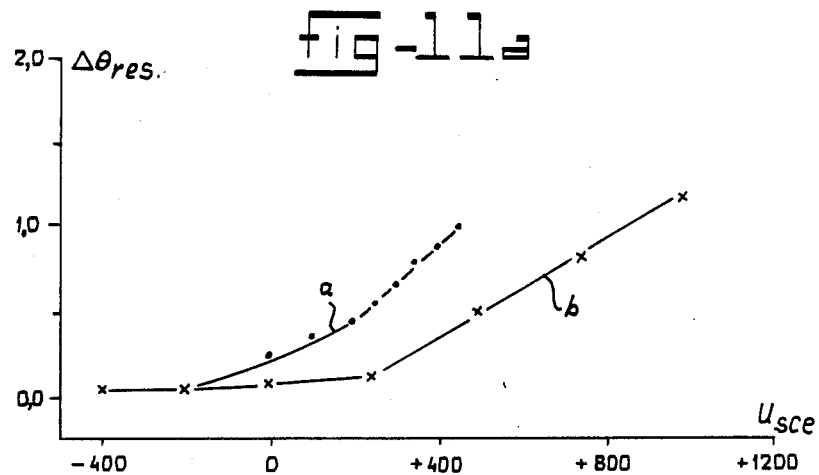
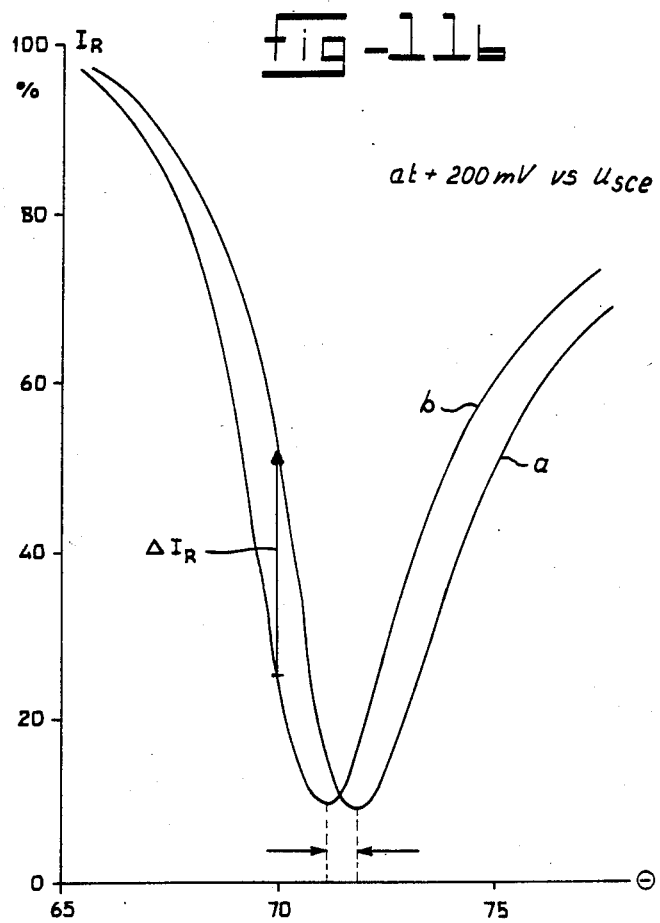

METHOD AND APPARATUS FOR DETECTING LOW CONCENTRATIONS OF (BIO) CHEMICAL COMPONENTS PRESENT IN A TEST MEDIUM USING SURFACE PLASMON RESONANCE

The invention relates to a method for detecting low concentrations of at least one (bio-)chemical component present in a test medium in a test cell, having a metal layer as sub wall with an external prism, using the surface plasmon resonance effect, in which a light ray polarized in the plane of incidence is coupled in via the prism and, after attenuated total reflection, is coupled out and the intensity thereof is measured, the incidence angle position of the resonance curve therein being determined under influence of the change, caused by the component, in the dielectric constant of the test medium near the metal layer.

The invention also relates to an apparatus for detecting low concentrations of at least one (bio-)chemical component present in a test medium, using the surface plasmon resonance effect, which apparatus is provided with a test cell for the test medium having a metal layer as sub wall with an external prism, a monochromatic light source for coupling in via the prism a light ray polarized in the plane of incidence in order to excite a surface plasmon wave in the metal layer, and at least a detector for measuring the intensity occurring with attenuated total reflection in the light ray coupled out, the incidence angle position of the resonance curve therein changing under the influence of the change, caused by the component, in the dielectric constant of the test medium near the metal layer.

From the article entitled "Surface plasmon resonance for gas detection and biosensing" by C. Nylander, et al in "Sensors and actuators", 4 (1983), pages 299–304 it is known that the so called surface plasmon resonance effect is used for gas detection. With this, small variations in the dielectric constant of a gaseous medium can be measured. These variations are, for example, a consequence of the change in the composition of the medium.

In the case of the method and apparatus described in the abovementioned article, a surface plasmon wave can be excited in the thin metal layer, which forms a sub wall of the test cell, by means of a light ray polarized in the plane of incidence. The thickness of the metal layer or film on the prism has to be very thin. The excitation takes place at a particular angle of incidence, and this can be measured by detecting the intensity of the attenuated, totally reflected light with a varying angle of incidence. A change in the composition of the test medium or in the content of the component under investigation in the test medium results in a change in the dielectric constant, as a result of which the resonance curve shifts to another resonant angle of incidence. This can be used for a quantitative detection, the intensity of the reflected light being measured at a fixed angle. The most sensitive method of detection is to measure the intensity at the edge of the resonance curve since a shift of the surface plasmon resonance curve then will cause the largest change in signal.

A problem in the abovementioned known method and apparatus is the low selectivity, and the fact that only one component can be measured at a time.

The object of the invention is to eliminate this disadvantage and to provide a method and apparatus with which very low concentrations of (bio-)chemical components in a test solution or medium can be detected simultaneously in a selective manner.

According to the invention, this is achieved in a method of the type mentioned in the introduction, such that an adjustable selector is applied to the metal layer in order to influence the incidence angle position of the resonance curve, through which the concentrations or concentration changes of one or more components in the test medium can be simultaneously determined through one or more differential measurements because a preferential association and therefor a higher concentration at the metal layer of one component above another is brought about.

At the same time, according to the invention, this is achieved in an apparatus of the type mentioned in the introduction such that the test cell is embodied with an adjustable selector at the metal layer in order to influence the incidence angle position of the resonance curve, through with the concentrations or concentration changes of one or more components in the test medium can be determined simultaneously via one or more differential measurements because a preferential association and therefor a higher concentration at the metal layer of one component above another is brought about.

It is known per se from the article entitled "Surface plasmons as a probe of the electrochemical interface" of J. G. Gordon II et al from the periodical "Surface Science" vol. 101, 1980 page 499–506, North-Holland Publishing Co., Amsterdam, to influence the incidence angle position of the resonance curve with the aid of a variable electrode potential and thereby to determine subsequently certain components. As a result of this electrochemical potential dependence, the concentration of free electrons near the interface and thereby the optical dielectric constant is indeed influenced. The sensitivity, realised thereby, however, is far less than the sensitivity of present invention. The selective character and thereby the possibility of differential measurements, for determining the concentrations or concentration changes of one or a plurality of components in the test medium simultaneously, are not mentioned in said article. At the same time, in this know apperatus use is made of the usual cumbrous method for changing the angle of incidence of the incoming light ray via a stepping motor and a rotating table.

The invention will be explained inmore detail on the basis of some embodiments with reference to the drawings, in which the same elements in the different figures are indicated with the same reference numerals, and wherein:

FIG. 3 shows a diagram of a knownmeasuring apparatus;

FIGS. 11a and 11b show respectively graphs of the angle of resonance against potential of two solutions and of the resonance curve of the same solutions at one potential.

Figure 1:
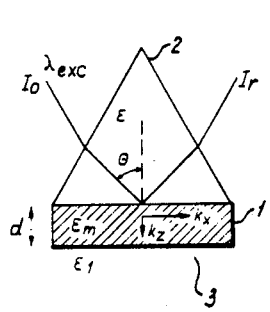
FIG. 1 shows a diagram of the known surface plasmon wave excitation according to the Kretschmann configuration.

Surface plasmon resonance is an optical technique which has been known for a short time in the field of examination for chemical components. Under the correct conditions, the reflectivity of a thin metal layer will be sensitive to variations in the medium on one side of the metal layer. A surface plasmon wave can be regarded as a density wave of the free electron plasma. The type of plasmon wave which is of importance in this connection is the non-radiating surface plasmon wave. Such a surface plasmon wave can be excited only by incident monochromatic light which is polarized in the plane of incidence. In this connection, reference is made to FIG. 1. Here 1 indicates a metal layer, 2 indicates a prism, 3 indicates a test medium or test soultion, Io indicates a coupled-in light ray and Ir indicates the light ray coupled out after reflection.

Figure 2:
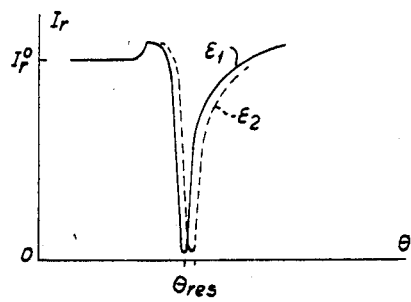
FIG. 2 shows a surface plasmon resonance (SPR) curve which represents the reflected intensity as a function of the angle of incidence of a light ray for two values of the dielectric constant.

For a particular angle of incidence of the light coupled in via the prism, surface plasmons will be resonantly excited. This is observed on measuring the intensity of the attenuated totally reflected light as a very sharp minimum in the light reflection when the angle of incidence is varied, as is indicated in FIG. 2. Now, a change in the content of the compound or component to be examined in a medium results in a change in the dielectric constant (from $\epsilon_1$ to $\epsilon_2$), as a result of which the entire resonance curve shifts to another resonant angle of incidence (FIG. 2). This change in position will occur only for a change in the dielectric constant at a very short distance from the metal layer, in the order of the excitation wavelength.

Although small variations in the dielectric constant of a medium can be measured with this method, the selectivity is low or even non-existent. By making use of an adjustable selector at the metal layer a stimulated (preferential) association of the components under examination can be obtained in the presence of said adjustable selector and the selectivity can be increased correspondingly. Such an adjustable selector for example is a variable potential or a (bio-)chemical affinity ligand, such as an antibody, DNA-probe, crown-ether, and so on. The preferential association then is preferential adsorption or a preferential binding.

By applying a variable potential difference, related to the components to be measured, between the metal layer and the test solution, a plurality of components can be adsorbed subsequently at the metal surface. Since the adsorption is usually dependent on the potential, a certain selectivity is obtained as a result of this. Since the surface plasmon resonance occurs at the metal-solution interface, the sensitivity of the measurement will also increase considerably as a result of the local increase in concentration which occurs during adsorption.

For the said electrochemically stimulated adsorption it is necessary for the test medium to be conductive. For this purpose, an electrolyte solution can be employed in which the components to be examined or the adsorbates are dissolved.

FIG. 3 shows diagrammatically a surface plasmon resonance measuring apparatus with variable potential adjustment. Using the Kretschmann configuration, a surface plasmon wave is excited at the surface of the metal layer 1. The metal layer joined to the prism 2 is coupled via a brass ring (not shown), coated with an electric conductor f.i. gold, and a sealing ring to the test cell 6. Said test cell contains the test medium 3. A reference potential Uref is formed by means of a reference electrode 9 (for example, Ag/AgCl or SCE) with internal salt bridge. The variable potential difference is applied between the metal layer, which functions as working electrode, and the reference electrode. Any passage of current takes place between the working electrode 1 and the platinum counter electrode 10.

Further, 12 indicates a polarized laser, 13 a neutral density filter; and 14 a stepping motor for causing the rotating table 15 with the test cell provided thereon in the Kretschmann configuration to rotate. The three electrodes mentioned above are connected to a potentiostat 16 which is fed by a function generator 21. The reflected light passes through a lens 17 and is incident on the detector 18, both being attached to the rotation spindle of the rotating table. The output signal of the detector 18 is fed to a radiometer 19 which in turn drives a recorder 20.

Figure 4A:
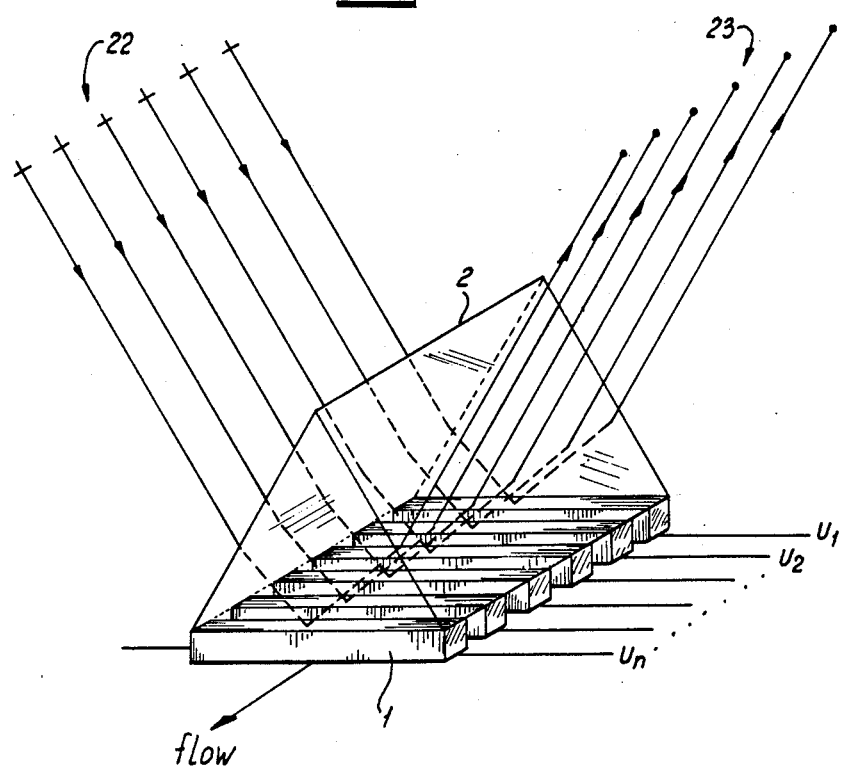
FIG. 4a shows a perspective view of the measuring apparatus according to the invention having an array-like implementation of the metal layer and of the light source detector arrangement.
Figure 4B:
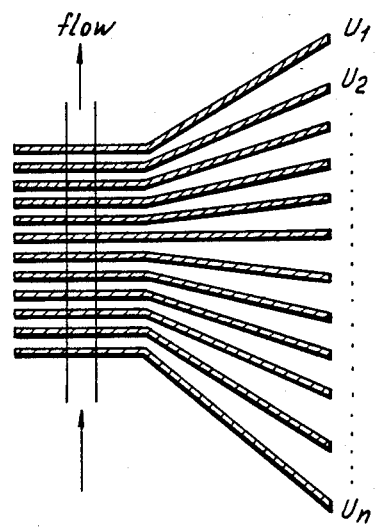
FIG. 4b shows a plan view of the array of metal layers and their connections.

The selectivity can be further improved by using, instead of a continuous metal layer, an array or grouping of metal ayer strips 1 to which various potentials are applied. In this connection, reference is made to FIG. 4a. The light rays to be coupled in are generated with an array of light sources 22 and the reflected light rays are then detected with a linear photodiode—or CCD—array 23. FIG. 4b shows a plan view of the array of metal layer strips connected to a number of connections to which various potentials U1 to Un are applied. In this manner the concentrations or concentration changes of one or more components present in the test medium can be measured simultaneously in a selective manner by means of difference measurements without having to scan the potential.

In addition, this has the advantage that changes in dielectric constant of the test medium itself or the solvent (eluent), which are not the result of a concentration change of adsorbable components, are eliminated. This can be achieved by choosing a potential (as reference) at which the expectation is that no adsorption of any component whatsoever will take place at it. If changes are nevertheless produced in the solvent or test medium, the signal change at said reference potential will be equal to the signal change of the components to be measured.

Figure 5:
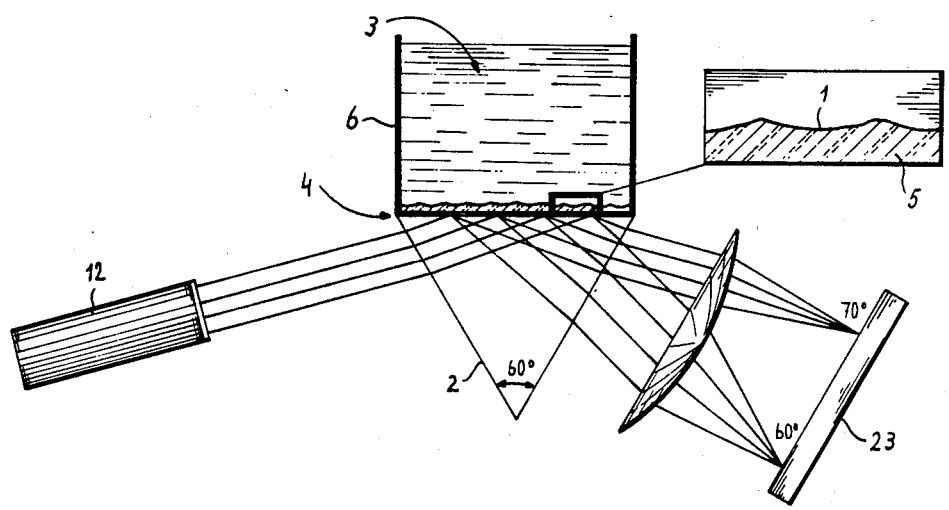
FIG. 5 shows an embodiment of the measuring apparatus according to the invention.
Figure 2:
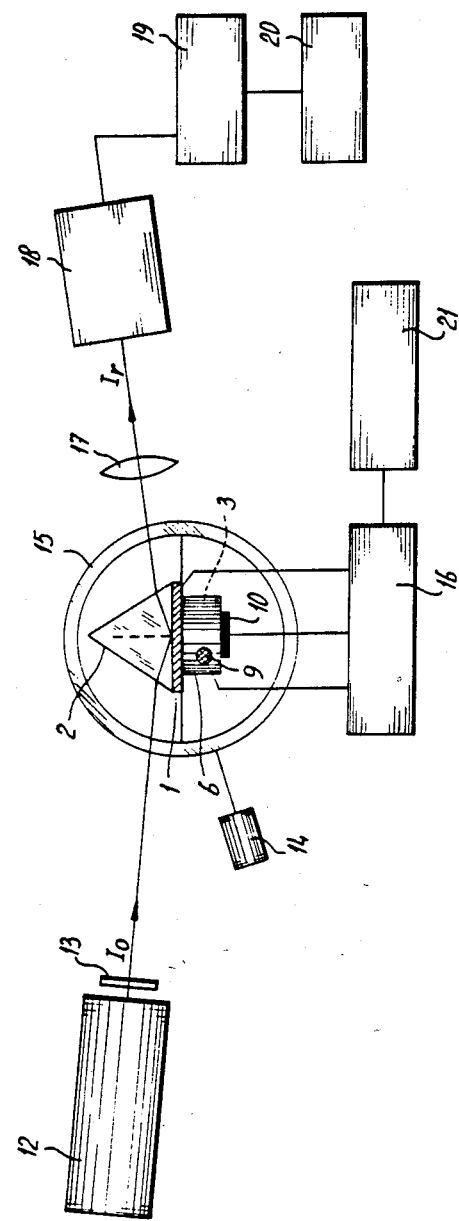

In FIG. 5 an advantage arrangement is indicated in which the stepping motor 14 and rotation table 15 of FIG. 3 are eliminated. Based on a mutually fixed position of one light source 12, for example an AlGaAs semiconductor laser, and the test cell 6, however, a range of variable angles of incidence of the light ray can indeed be obtained, f.i. from 60° to 70°. The laser 12 emits a beam of parallel light rays which via the prism 2 are coupled in in the transparent polarisation-free slide 5, consisting of glass or plastic, which is coupled via an immersion oil film 4 to the prism 2. The slide 5 at the side of the test medium 3 is provided with a number of isolated parallel grooves, the curvatures of which are mutually precise and identical and the longitudinal direction of which is transverse to the direction of the beam of light rays. A metal layer 1, f.i. gold, is provided on the surface of the grooves in the slide 5. On said metal layer the light rays, in dependence on the location in the groove, enter under different angles of incidence. The light rays coupled out after total reflection are focussed via a cylindrical lens onto a row of light detectors, f.i. CCD's. The position of the resonant angles of incidence are now determined via differential measurements for one or more components in dependence of the adjustable potential.

Figure 6:
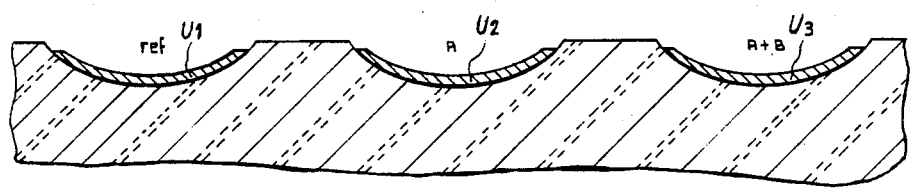
FIG. 6 shows a diagram of a number of measuring ranges with an adjustable potential as selector.

FIG. 6 indicates in which manner via differential measurements the resonant angles of incidence and thereby a plurality of components in the test medium can be determined with the aid of a variable potential. The potential regions oa, ab, bc, and cd can subsequently be established on the potential axis, which regions respectively correspond with the resonant angles of incidence $\theta res_{ref}$, $\theta res_A$, $\theta res_{A+B}$, and $\theta res_{A+B+C}$ and thereby with the reference component (test medium f.i.), component(s) A, A+B, and A+B+C.

Figure 7A:
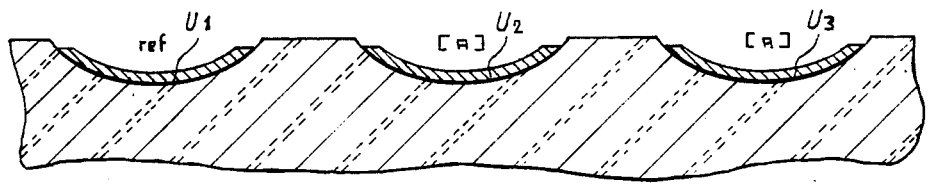
FIGS. 7a through 7c show variants of the metal layers having different selectors respectively.
Figure 7B:
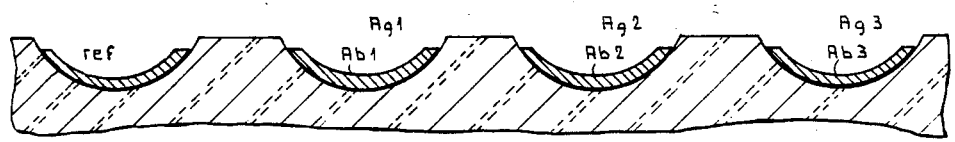
Figure 7C:
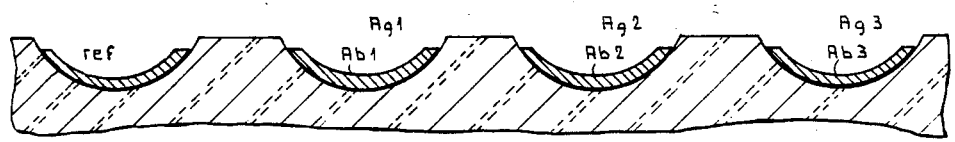

FIGS. 7a, 7b, 7c show several embodiments with the aid of which, and together with an adjustable selector at the metal layer, a plurality of components (or the concentration of one component in various samples) can be determined.

FIG. 7a indicates that different potentials U1, U2, and U3 are applied to the mutually isolated metal layers in adjacent (groups of) grooves, which potentials respectively correspond with the reference component, component A, and component A+B. Said components A, B, and measurements.

FIG. 7b indicates that, with the aid of different potentials U1, U2, and U3 at the metal layers in the adjacent grooves, the various concentrations of component [A] in various sample in the medium can be determined with respect to the reference component.

FIG. 7c indicates that, instead of an adjustable potential as selector, now an array of (bio-)chemical selective affinity ligands, such as f.i. an antibody (Ag), a DNA-probe, a (lipo) polysaccharide, can be used as selector. Thereby interactions or preferential bindings for example between antibodies (Ab) and antigenes (Ag) can be examined. In this case, then subsequently no antibody and antibodies Ab1, Ab2 and Ab3 (f.i. polio virus, tubercil bacil, measles) are fixedly adsorbed to the metal layers of adjacent grooves, and the antigenes Ag1, Ag2, and Ag3 then can be examined via preferential bindings in the test medium.

Figure 7D:
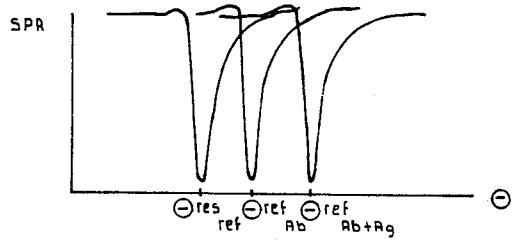
figure 7d shows a graph explaining FIG. 7c.

In FIG. 7d for one combination Ab, Ag the subsequent positions of the resonant angles of incidence are indicated respectively without affinity ligand, with Ab, with Ab+Ag. It is obvious that the interactions can also be examined in a reverse manner i.e. that instead of antibodies, the antigenes are fixedly adsorbed to the metal layers. It is also possible that DNA- or RNA-probes can be used as selectors in order to examine the presence of homologous DNA.

Figure 8A:
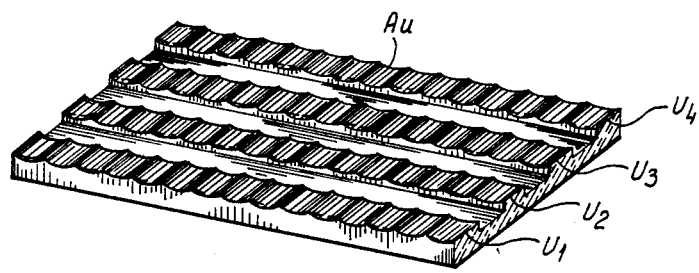
FIGS. 8a through 8c show further variants of the metal layers having different selectors respectively.
Figure 8B:
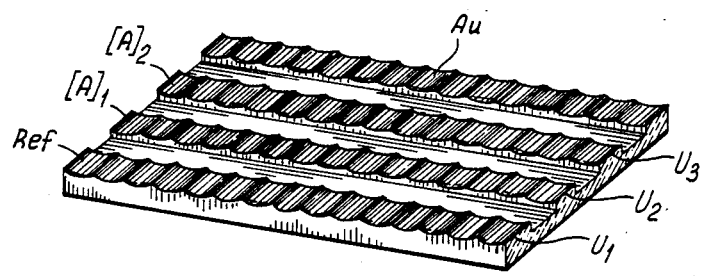
Figure 8C:
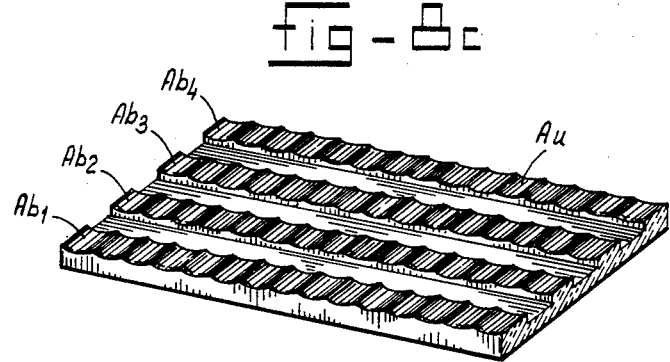

FIGS. 8a, 8b and 8c show further variants of said grooves in relation with FIGS. 7a, 7b and 7c. Each groove now consist of a row of interrupted (mutually isolated) groove portions, the longitudinal direction of which is still transverse to the beam of light rays as in FIG. 5. The connection of the potentials U1, U2, U3, . . . is however different with respect to FIG. 7. Said selectors are now applied each to a metal strip consisting of adjacent groove portions. Through this system two advantages are obtained. First, by irradiating a plurality of curvatures, i.e. a plurality of (interrupted) grooves, an interference pattern comes about in the coupled-out light. Said pattern can be used as internal calibration in order to assist in determining the shift of the resonant angle due to changes in the dielectric constant at the metal surface. Second, it is possible through this system of interrupted grooves to determine a plurality of component concentrations or -changes simultaneously or quickly in succession by using a CCD-(matrix) camera.

Figure 9:
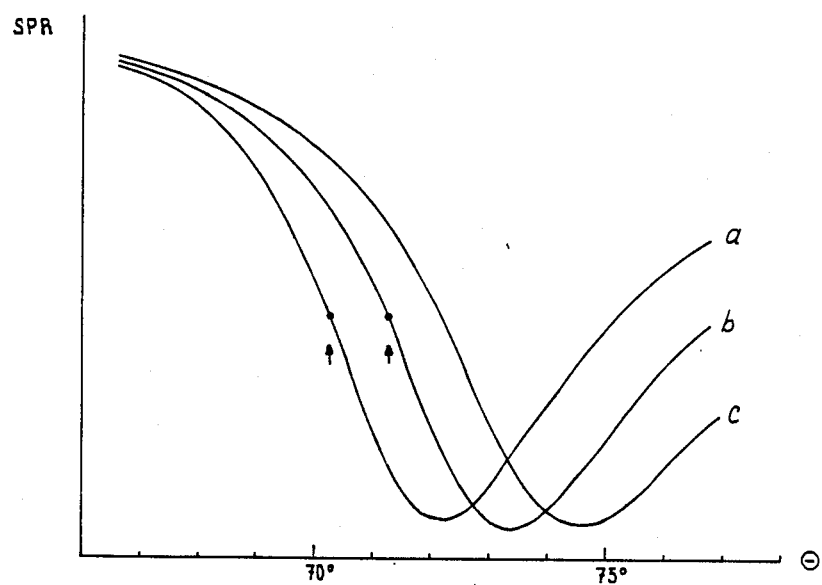
FIG. 9 shows a graph of surface plasmon reference (SPR) against angle of incidence of one metal layer with and without selector.

FIG. 9 shows the mesuring results of an antigene/antibody interaction through surface plasmon resonance (SPR). The three curves represent SPR reflections at a gold film in contact with: (a) a reference (PBS buffer) solution; (b) a fixedly adsorbed antibody (human IgG); and (c) said antibody in preferential binding with antigene (anti-IgE).

Figure 10:
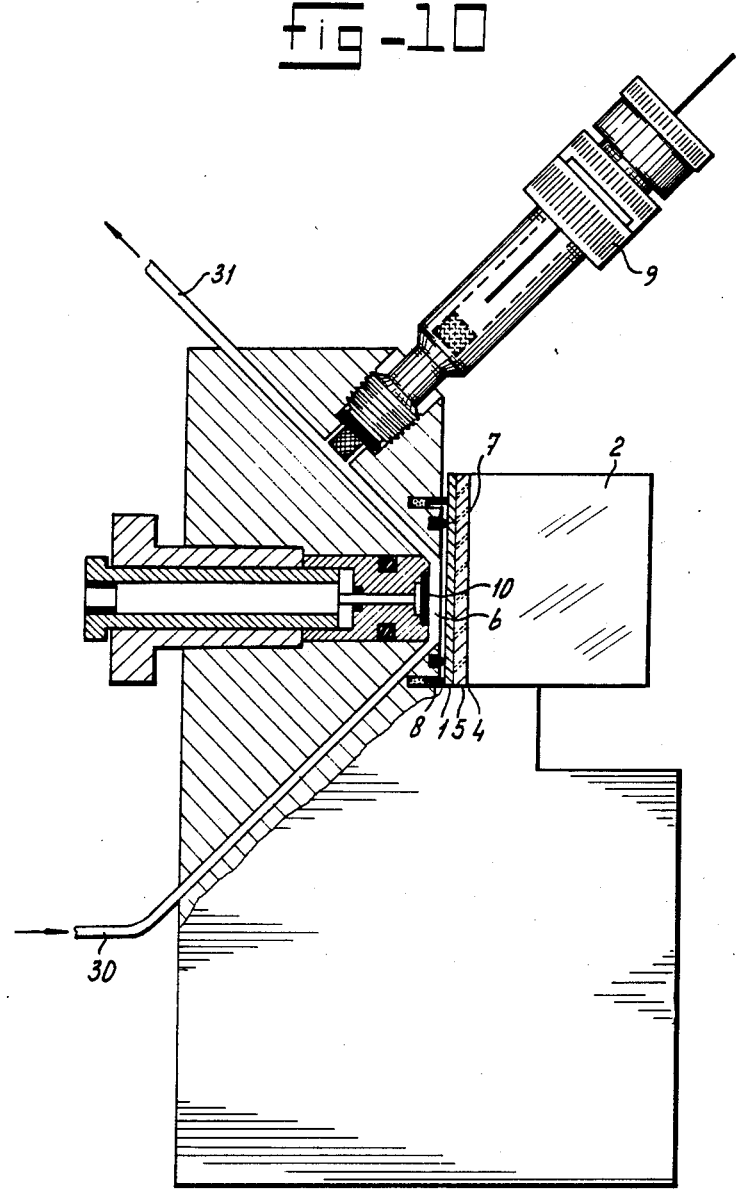
FIG. 10 shows an embodiment of the measuring apparatus as a continuous-flow detector.

FIG. 10 gives an example of a measuring apparatus according to the invention which is constructed as a continuous-flow detector. The test medium in which the component under examination has been taken up is supplied and removed via the conduits 30 and 31. The test cell or the test volume 6 is again bounded on one side by the metal layer 1 which functions as working electrode. This metal layer is again deposited on a slide 5 consisting of glass or plastic, which is coupled via immersion oil 4 to the prism 2. 7 indicates a sealing ring and 8 indicates a brass connecting contact of the metal layer. 9 and 10 again indicate the reference electrode and the counterelectrode. In a variant, such an apparatus can be implemented as a wall-jet detector.

The result of a number of measurements will now be discussed. Measurement is always carried out with metal layers or films of optimum thickness, i.e. films whose surface plasmon resonance curve is as narrow and deep as possible. For gold this thickness is approx. 450 Å and for silver approx. 400 Å. Plasmon resonance curves recorded for aqueous solutions are less deep, are wider and have a greater angle of resonance. In spite of the somewhat narrower resonance peak in the case of silver, it is advantageous to use gold as the electrode material for the surface plasmon resonance measurement since gold is more inert than silver. This is the case, in particular, at high electrode potentials. The potential dependency of the SPR curve is clearly evident from measurements. The reason is that potential change influences the distribution of the electron density at the metal-test medium interface and the structure of the ionogenic double layer.

Measurements ondifferent salt solutions using a gold film and a silver film as metal layer exhibit the said potential-dependent effect.

Adsorption of iodine on a gold film: measurements have been carried out with various solutions of potassium iodide in 0.1 M $K_2SO_4$. In FIG. 11a the angle of resonance is plotted as a function of the potential for a solution of $10^{-5}$ M KI in 0.1 M $K_2SO_4$ (curve a) and for a 0.1 M $K_2SO_4$ *solution without KI (curve b). In all the series of measurements, larger changes in $\theta res$ with Usce were observed with iodide solutions than in the case of solutions without iodide. This change became greater as the concentration of iodide increased. FIG.* 11b shows the two resonance curves for the same solution for one potential.

The minimum concentration of iodide determined in the measurements was approx. 30 ppb. On the basis of further measurement results and on the basis of calculations, it can be stated that the method according to the invention is still more sensitive than indicated above. Under the same conditions as the iodide measurements, no changes in signal were measured for solutions of $10^{-3}$ M KCl or KBr, which demonstrates the extraordinary selectivity of this technique.

The method and apparatus outlined may be used, as stated, for the determination of halides, in particular iodide, but also for further substances such as organic compounds.

The response time can be shortened by constructing the measuring apparatus as a continuous-flow detector with a small detector volume ($<1$ $\mu l$). At the same time, this limits the widening of the (chromatographic) peak in the detector, in other words the dilution in the detector, of a sample or component injected into the carrier medium to a minimum. As a result, this is an excellent technique for high-pressure liquid chromatography and flow-injection analysis.

We claim:

1. In a method for detecting low concentrations of at least one chemical component present in a test medium in a test cell, the test cell having a metal layer as sub wall with an external glass prism, using the surface plasmon resonance effect in which a light ray polarized in the plane of incidence is coupled in via the prism and, after attenuated total reflection, is coupled out and the intensity thereof is measured, the incidence angle position of the resonance curve being determined under the influence of change caused in the dielectric constant of the test medium near the metal layer by the chemical component, the improvement comprising providing the metal layer as an array of metal layer strips, each strip being provided with a different selector from a selector array of one type, and simultaneously determining concentrations or concentration changes of one or more components in the test medium through one or more differential measurements caused by a preferential association between each component and such a selector.

2. The method according to claim 1, wherein the selector is a variable potential thorugh which, in the differential measurement, a potential-dependent preferential adsorption of the one component above the other is achieved.

3. The method according to claim 1 further comprising applying various adjustable potentials to said array of metal layer strips, simultaneously coupling in several light rays corresponding to the strips, and measuring said light rays reflected by the separate metal layer strips.

4. The method according to claim 2 further comprising coupling in a single beam of parallel light rays under a fixed angle of incidence, providing the interface of the metal layer and the test medium with a plurality of parallel grooves, the longitudinal direction of which is transverse to the direction of the beam of light rays such that a fan of light rays is coupled out of the prism under different angles, and measuring the intensity of said rays by an array of light detectors.

5. The method according to claim 1, wherein the selector comprises a plurality of different chemical affinity ligands which are fixed in an array to the metal layer, through which in the differential measurements and affinity ligand-dependent preferential association is achieved.

6. In an apparatus for detecting low concentrations of a least one chemical component present in a test medium using the surface plasmon rresonance effect, which apparatus is provided with a test cell for the test medium having a metal layer as sub wall with an external prism, a monochromatic light source for coupling in via the prism a light ray polarized in the plane of incidence in order to excite a surface plasmon wave in th metal layer, and at least one detector for measuring the intensity occurring with attenuated total reflection in the light ray coupled out, the incidence angle position of the reference curve changing due to the change in the dielectric constant of the test medium near the metal layer caused by the chemical component, the improvement comprising providing the metal layer as an array of metal layer strips, that each strip is provided with a different selector from a selector array of one type, and including means for simultaneously determining through one or more differential measurements due to a preferential association between one component and such a selector concentrations or concentration changes of one or more components in the test medium.

7. The apparatus according to claim 6, wherein the selector comprises a number of different potentials applied between a reference electrode and the separate metal layer strips, the light source comprises a corresponding light source array and the detector comprises a photo diode array, a plurality of lights rays being coupled in simultaneously and coupled out after reflection.

8. The apparatus according to claim 6, wherein the selector comprises an array of chemical affinity ligands which are fixed to the metal layer strips.

9. The apparatus according to claim 8, wherein the chemical affinity ligands are selected from the group consisting of antibodies and antigens, such that in the test medium various antigens or antibodies, respectively, can be determined.

10. The apparatus according to claim 8, wherein the array of chemical affinity ligands are selected from the group consisting of DNA-probes and RNA-probes, such that in the test medium homologous DNA can be determined.

11. The apparatus according to claim 6, wherein the light source emits a beam of parallel light rays, said beam being coupled into the prism at a fixed angle, in the test cell the interface of the metal layer and the test medium comprises a plurality of parallel grooves, the longitudinal direction of which is transverse to the direction of the beam of parallel light rays, such that a fan of light rays coupled out under different angles is produced, and that an array of detectors is provided to measure the intensity of the coupled out light rays.

12. The apparatus according to claim 11, wherein, by simultaneous irradiation of two or more grooves, the coupled out light rays constitute a characteristic interference pattern, which can be used as an internal calibration to assist in determining the shift of the plasmon resonance curve.

* * * * *